US008089049B2

(12) United States Patent
Ohta et al.

(10) Patent No.: US 8,089,049 B2
(45) Date of Patent: Jan. 3, 2012

(54) RADIATION IMAGE CAPTURING SYSTEM, APPARATUS FOR SUPPLYING IMAGE CAPTURING INSTRUCTION INFORMATION, PROGRAM, METHOD FOR SUPPLYING IMAGE CAPTURING INSTRUCTION INFORMATION, AND RADIATION IMAGE CAPTURING METHOD (75) Inventors: Yasunori Ohta, Yokohama (JP);
Naoyuki Nishino, Minami-ashigara (JP);
Naoki Mochizuki, Minami-ashigara (JP); Daiki Harada, Minami-ashigara (JP); Hiroshi Fukuda, Minato-ku (JP);
Eiichi Kito, Minami-ashigara (JP);
Kazuharu Ueta, Suginami-ku (JP)

(73) Assignee: Fujifilm Corporation, Tokyo (JP)

( * ) Notice: Subject to any disclaimer, the term of this patent is extended or adjusted under 35 U.S.C. 154(b) by 347 days.

(21) Appl. No.: 12/391,835

(22) Filed: Feb. 24, 2009

(65) Prior Publication Data
US 2009/0212223 A1 Aug. 27, 2009

(30) Foreign Application Priority Data

Feb. 26, 2008 (JP) .................................. 2008-044637
Feb. 26, 2008 (JP) .................................. 2008-044638
Feb. 13, 2009 (JP) .................................. 2009-031494

(51) Int. Cl.
*G01T 1/24* (2006.01)

(52) U.S. Cl. .................................. 250/370.08; 250/371
(58) Field of Classification Search ............... 250/336.1, 250/370.08, 371, 580, 581, 582, 584, 587
See application file for complete search history.

(56) References Cited

U.S. PATENT DOCUMENTS

2002/0080918 A1* 6/2002 Sako ............................. 378/115
2004/0071263 A1* 4/2004 Motoki ........................... 378/98

FOREIGN PATENT DOCUMENTS

| JP | 2000-105297 A | 4/2000 |
| JP | 3494683 B2 | 2/2004 |
| JP | 2004-341910 A | 12/2004 |
| JP | 2006-247137 A | 9/2006 |

* cited by examiner

*Primary Examiner* — Mark R Gaworecki
(74) *Attorney, Agent, or Firm* — Sughrue Mion, PLLC (57) ABSTRACT A radiation image capturing system includes a plurality of image capturing apparatus having different specifications for capturing a radiation image of a subject, a plurality of processors having specifications corresponding to the specifications of the image capturing apparatus, for controlling the image capturing apparatus and processing radiation image information acquired from the image capturing apparatus, and a supply apparatus for supplying image capturing instruction information for the image capturing apparatus to one of the processors, which is selected depending on the specifications of the image capturing apparatus.

23 Claims, 7 Drawing Sheets

RADIATION IMAGE CAPTURING SYSTEM, APPARATUS FOR SUPPLYING IMAGE CAPTURING INSTRUCTION INFORMATION, PROGRAM, METHOD FOR SUPPLYING IMAGE CAPTURING INSTRUCTION INFORMATION, AND RADIATION IMAGE CAPTURING METHOD

BACKGROUND OF THE INVENTION

1. Field of the Invention

The present invention relates to a radiation image capturing system and radiation image capturing method for controlling a plurality of image capturing apparatus of different specifications with a processor that is selected according to image capturing instruction information to capture radiation images, an apparatus and method for supplying image capturing instruction information to a selected processor, and a program executed in a supply apparatus for supplying image capturing instruction information.

2. Description of the Related Art

In the medical field, there have widely been used radiation image capturing apparatus, which apply radiation to a subject and guide the radiation that has passed through the subject to a radiation conversion panel, which captures a radiation image from the radiation.

One known type of radiation conversion panel is a stimulable phosphor panel, which stores radiation energy representative of a radiation image in a phosphor. When the stimulable phosphor panel is irradiated with stimulating light, the phosphor emits stimulated light representative of the stored radiation image. The stimulable phosphor panel with the radiation image recorded therein is supplied to a reading apparatus, which reads the stored radiation image as a visible radiation image.

In sites where medical procedures are performed, such as operating rooms or the like, it is necessary to read recorded radiation image information immediately from a radiation conversion panel, for the purpose of quickly and appropriately treating the patient. As a radiation conversion panel which meets such a requirement, there has been developed a radiation conversion panel having a solid-state detector therein for converting radiation directly into electric signals, or for converting radiation into visible light with a scintillator, and then converting such visible light into electric signals in order to read the detected radiation image.

There are available in the art various types of image capturing apparatus having different specifications for capturing radiation images using radiation conversion panels, depending on the conditions of patients as subjects to be imaged, and image capturing conditions including regions of the body to be imaged. Such different image capturing apparatus are controlled by respective processors having specifications that correspond to the specifications of the image capturing apparatus. According to a known radiographic system, various image capturing apparatus and processors are connected to a radiology information system (RIS) by an in-house system. Image capturing instruction information representative of image capturing conditions set by the RIS, which include patient information, image capturing methods, body regions to be imaged, radiation dosage levels, etc., is supplied to the processors, which then control corresponding image capturing apparatus in order to capture radiation images (see Japanese Laid-Open Patent Publication No. 2006-247137).

When a doctor sets image capturing instruction information using the RIS, the doctor sets image capturing instruction information for each image capturing apparatus to be used. If the doctor captures radiation images using a different image capturing apparatus, then since the doctor needs to set image capturing instruction information for each of the image capturing apparatus, the doctor often finds it tedious and time-consuming to set such image capturing instruction information. Furthermore, if an image capturing apparatus designated by the doctor fails to operate, or is undergoing preparations and is not ready for use, then the radiological technician on site needs to change the image capturing apparatus, i.e., change the image capturing instruction information on site.

If image capturing instruction information is supplied from the RIS to a predetermined processor, then while the predetermined processor is currently dealing with an image capturing apparatus or processing radiation image information acquired from an image capturing apparatus, the predetermined processor is unable to handle the image capturing instruction information, until the process currently being performed thereby is terminated.

Some general network systems are configured to distribute loads among a plurality of processors connected to the network. For example, the printing system disclosed in Japanese Laid-Open Patent Publication No. 2004-341910 comprises a host apparatus having a distributed printing function and a plurality of image forming apparatus, wherein the host apparatus and the image forming apparatus are connected to a network. If one of the image forming apparatus is incapable of printing images, then the host apparatus transfers print data to another image forming apparatus, which is capable of printing images.

However, the printing system disclosed in Japanese Laid-Open Patent Publication No. 2004-341910 is not premised on use of a plurality of image forming apparatus having different specifications, each of which are connected to the network. Rather, Japanese Laid-Open Patent Publication No. 2004-341910 merely discloses that, if a selected one of the image forming apparatus of similar specifications is incapable of printing images, then another one of the image forming apparatus may be selected to print images.

SUMMARY OF THE INVENTION

It is an object of the present invention to select a processor having specifications corresponding to the specifications of an image capturing apparatus, and supply image capturing instruction information for capturing a radiation image efficiently.

Another object of the present invention is to select a processor, which is capable of performing a processing sequence, and having specifications corresponding to the specifications of an image capturing apparatus, and supply image capturing instruction information for processing radiation image information efficiently.

A radiation image capturing system according to an aspect of the present invention comprises a plurality of image capturing apparatus having different specifications for capturing a radiation image of a subject, a plurality of processors having specifications corresponding to the specifications of the image capturing apparatus, for controlling the image capturing apparatus and processing radiation image information acquired from the image capturing apparatus, and a supply apparatus for supplying image capturing instruction information for the image capturing apparatus to one of the processors, which is selected depending on the specifications of the image capturing apparatus.

Further, in a supply apparatus for supplying image capturing instruction information according to the present invention, in the case that a plurality of image capturing apparatus having different specifications for capturing a radiation image of a subject, and a plurality of processors having specifications corresponding to the specifications of the image capturing apparatus, for controlling the image capturing apparatus and processing radiation image information acquired from the image capturing apparatus, are provided, the supply apparatus selects the processors depending on the specifications of the image capturing apparatus, and supplies image capturing instruction information pertaining to the image capturing apparatus to the selected processors.

Furthermore, in a program according to the present invention, in the case that a plurality of image capturing apparatus having different specifications for capturing a radiation image of a subject, and a plurality of processors having specifications corresponding to the specifications of the image capturing apparatus, for controlling the image capturing apparatus and processing radiation image information acquired from the image capturing apparatus, are provided, the program is executed in a supply apparatus for supplying, from the supply apparatus, image capturing instruction information pertaining to the image capturing apparatus to the processors, and the program comprises:

a step of selecting the processors depending on the specifications of the image capturing apparatus, and a step of supplying image capturing instruction information pertaining to the image capturing apparatus to the selected processor.

Still further, in a method for supplying image capturing instruction information according to the present invention, in the case that a plurality of image capturing apparatus having different specifications for capturing a radiation image of a subject, and a plurality of processors having specifications corresponding to the specifications of the image capturing apparatus, for controlling the image capturing apparatus and processing radiation image information acquired from the image capturing apparatus, are provided, the method comprises the steps of:

selecting the processors depending on the specifications of the image capturing apparatus, and supplying, from the supply apparatus, image capturing instruction information pertaining to the image capturing apparatus to the selected processor.

Still further, in a method for capturing a radiation image according to the present invention, in the case that a plurality of image capturing apparatus having different specifications, and a plurality of processors having specifications corresponding to the specifications of the image capturing apparatus, are provided, the method comprises the steps of:

selecting the processors depending on the specifications of the image capturing apparatus;

supplying image capturing instruction information from a supply apparatus to the selected processor;

capturing a radiation image of a subject using the image capturing apparatus, by the processor controlling the image capturing apparatus according to the image capturing instruction information; and acquiring radiation image information from the image capturing apparatus and performing image processing thereon using the processor.

In the above inventions, image capturing instruction information is supplied to one of the processors, which is selected depending on the specifications of the image capturing apparatus, and the selected processor controls the corresponding image capturing apparatus for thereby efficiently capturing a radiation image of the subject.

A radiation image capturing system according to another aspect of the present invention comprises a plurality of image capturing apparatus having different specifications for capturing a radiation image of a subject, a plurality of processors having specifications corresponding to the specifications of the image capturing apparatus, for controlling the image capturing apparatus and processing radiation image information acquired from the image capturing apparatus, and a supply apparatus for selecting one of the processors having specifications that correspond to the specifications of the image capturing apparatus, and which is capable of performing a processing sequence for the image capturing apparatus, and supplying image capturing instruction information for the image capturing apparatus to the selected one of the processors.

Further, in a supply apparatus for supplying image capturing instruction information according to another aspect of the present invention, in the case that a plurality of image capturing apparatus having different specifications for capturing a radiation image of a subject, and a plurality of processors having specifications corresponding to the specifications of the image capturing apparatus, for controlling the image capturing apparatus and processing radiation image information acquired from the image capturing apparatus, are provided, the supply apparatus selects one of the processors depending on the specifications of the image capturing apparatus, and further which is in a state capable of performing processing, and supplies image capturing instruction information pertaining to the image capturing apparatus to the selected one processor.

Furthermore, in a program according to another aspect of the present invention, in the case that a plurality of image capturing apparatus having different specifications for capturing a radiation image of a subject, and a plurality of processors having specifications corresponding to the specifications of the image capturing apparatus, for controlling the image capturing apparatus and processing radiation image information acquired from the image capturing apparatus, are provided, the program is executed in a supply apparatus for supplying, from the supply apparatus, image capturing instruction information pertaining to the image capturing apparatus to the processors, and the program comprises:

a step of selecting one of the processors depending on the specifications of the image capturing apparatus, and further which is in a state capable of performing processing, and a step of supplying, from the supply apparatus, image capturing instruction information pertaining to the image capturing apparatus to the selected one processor.

Still further, in a method for supplying image capturing instruction information according to another aspect of the present invention, in the case that a plurality of image capturing apparatus having different specifications for capturing a radiation image of a subject, and a plurality of processors having specifications corresponding to the specifications of the image capturing apparatus, for controlling the image capturing apparatus and processing radiation image information acquired from the image capturing apparatus, are provided, the method comprises the steps of:

selecting one of the processors depending on the specifications of the image capturing apparatus, and further which is in a state capable of performing processing, and supplying, from the supply apparatus, image capturing instruction information pertaining to the image capturing apparatus to the selected one processor.

Still further, in a method for capturing a radiation image according to another aspect of the present invention, in the case that a plurality of image capturing apparatus having different specifications, and a plurality of processors having specifications corresponding to the specifications of the image capturing apparatus, are provided, the method comprises the steps of:

selecting one of the processors depending on the specifications of the image capturing apparatus, and further which is in a state capable of performing processing, and supplying, from the supply apparatus, image capturing instruction information to the selected one processor;

capturing a radiation image of a subject using the image capturing apparatus, by the one processor controlling the image capturing apparatus according to the image capturing instruction information; and acquiring radiation image information from the image capturing apparatus and performing image processing thereon using the one processor.

In accordance with the above inventions, one of the processors having specifications corresponding to the specifications of the image capturing apparatus, and which is capable of performing a processing sequence for the image capturing apparatus, is selected and supplied with the image capturing instruction information. The selected processor can control the corresponding image capturing apparatus in order to capture a radiation image efficiently, and can also process the acquired radiation image information efficiently.

The above and other objects, features, and advantages of the present invention will become more apparent from the following description when taken in conjunction with the accompanying drawings in which a preferred embodiment of the present invention is shown by way of illustrative example.

DESCRIPTION OF THE PREFERRED EMBODIMENT

Figure 1:
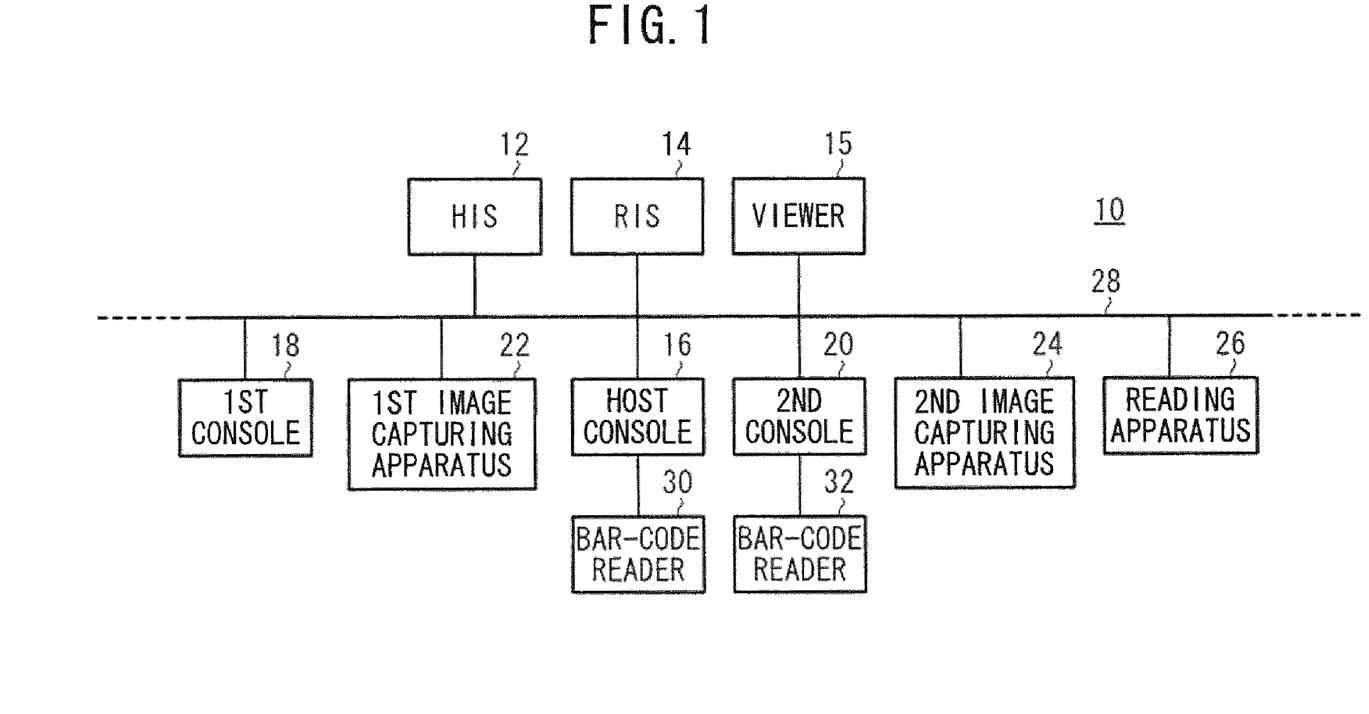
FIG. 1 is a block diagram of a radiation image capturing system according to an embodiment of the present invention.
Figure 2:
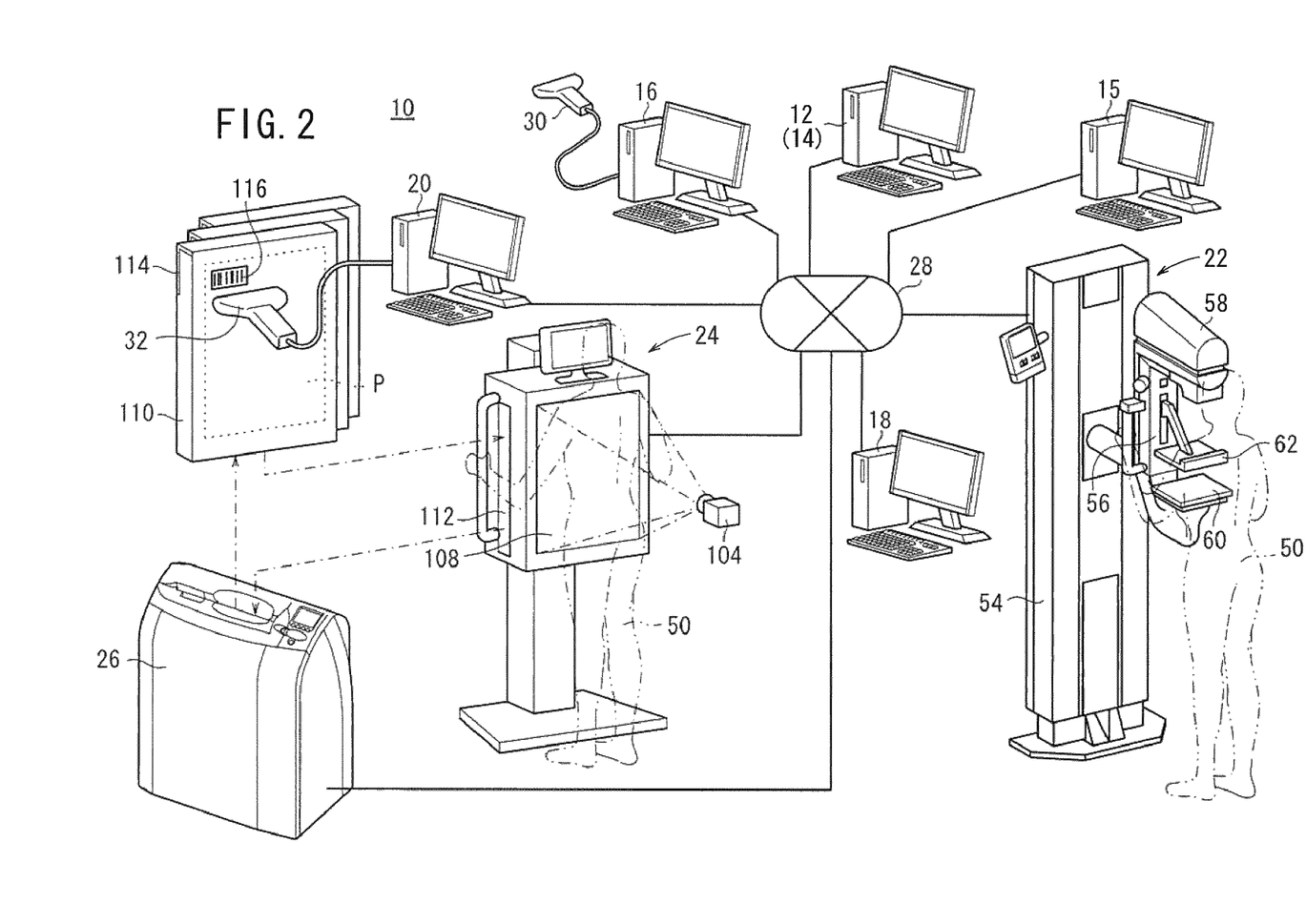
FIG. 2 is a schematic perspective view of the radiation image capturing system shown in FIG. 1.

FIGS. 1 and 2 show a configuration of a radiation image capturing system 10 according to an embodiment of the present invention. As shown in FIGS. 1 and 2, the radiation image capturing system 10 comprises a hospital information system (HIS) 12 for managing medical information in a hospital, a radiology information system (RIS) 14 for managing radiation image capturing processes performed in the radiological department of the hospital under the management of the HIS 12, a viewer 15 for displaying radiation images to be interpreted by a doctor for diagnosis, a host console 16 placed in a control room in close proximity to image capturing rooms in the radiological department, for managing various image capturing apparatus having different specifications through execution of a program stored in a non-illustrated memory, a first console 18 (processor) and a second console 20 (processor) placed in the control room for controlling particular image capturing apparatus, respectively, a first image capturing apparatus 22 controlled by the first console 18, a second image capturing apparatus 24 controlled by the second console 20, and a reading apparatus 26 controlled by the second console 20 for reading radiation image information captured by the second image capturing apparatus 24. The above components of the radiation image capturing system 10 are interconnected by an in-house network 28 in the hospital. If necessary, other consoles, other image capturing apparatus, and other components may also be connected to the in-house network 28.

The host console 16 executes the aforementioned program and acquires patient information such as the name, gender, age, etc., of a patient, which has been set using the HIS 12, and image capturing instruction information such as a method of capturing a radiation image, a body region to be imaged, and an image capturing apparatus to be used to capture the radiation image, which has been set by the doctor or radiological technician using the RIS 14 through the in-house network 28, and which supplies the acquired information to the first console 18 or the second console 20. The host console 16 may be programmed to perform a processing sequence of the first console 18 or the second console 20. If the host console 16 is programmed to perform the processing sequence of the first console 18 or the second console 20, then since the first console 18 or the second console 20 can be dispensed with, the radiation image capturing system becomes less costly. To the host console 16 and the second console 20, there are connected respective bar-code readers 30, 32 for acquiring ID information for identifying a radiation conversion panel, described later, to be used in the second image capturing apparatus 24.

Figure 3:
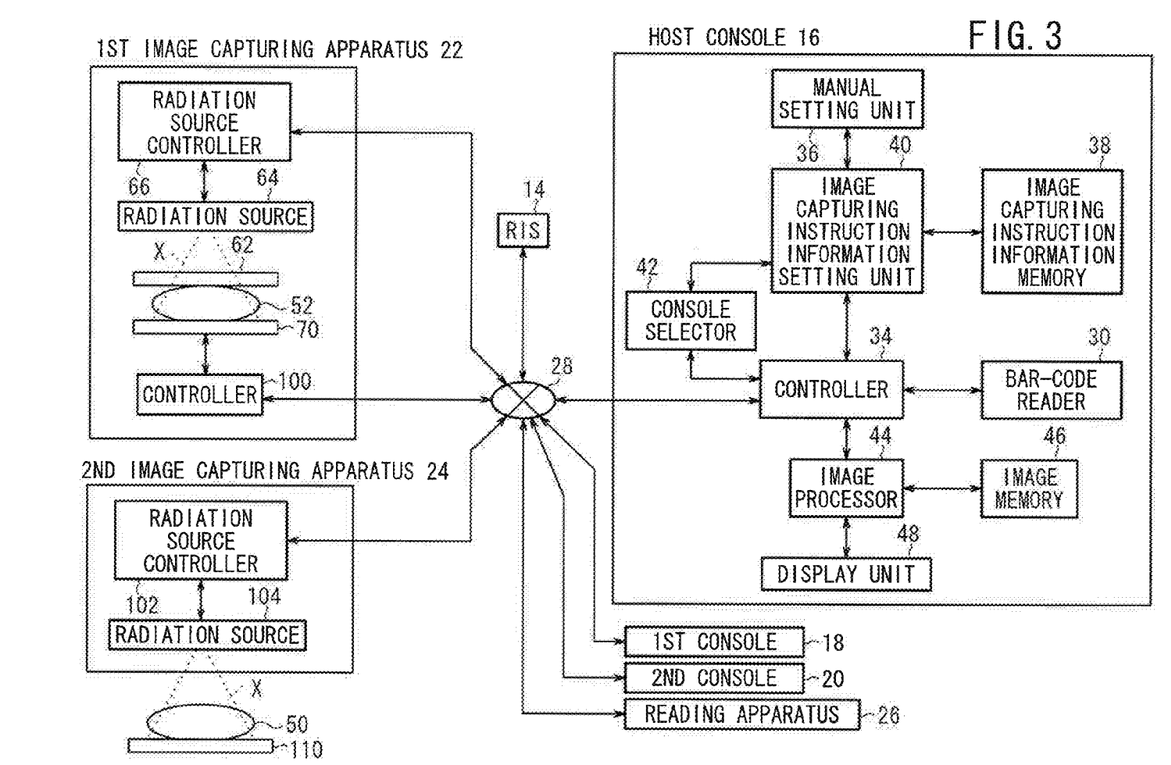
FIG. 3 is a block diagram of an assembly of a host console, a first image capturing apparatus, and a second image capturing apparatus shown in FIG. 1.

FIG. 3 shows in block form an assembly of the host console 16, the first image capturing apparatus 22, and the second image capturing apparatus 24.

The host console 16 includes a controller 34, which sends information to and receives information from the RIS 14, the first console 18, the second console 20, the first image capturing apparatus 22, the second image capturing apparatus 24, and the reading apparatus 26. The host console 16 comprises a manual setting unit 36, an image capturing instruction information setting unit 40 for setting image capturing instruction information through the manual setting unit 36, or for receiving image capturing instruction information set by the RIS 14 and storing the image capturing instruction information in an image capturing instruction information memory 38, a console selector 42 for selecting the first console 18 or the second console 20 for processing radiation image information according to the set image capturing instruction information, and supplying the corresponding image capturing instruction information to the first console 18 or the second console 20, which has been selected, an image processor 44 for processing radiation image information acquired from the first image capturing apparatus 22 or the second image capturing apparatus 24, an image memory 46 for storing processed radiation image information, and a display 48 for displaying the radiation image information.

The first console 18 and the second console 20 have essentially the same functions as the host console 16, except for the controller 34 for acquiring image capturing instruction information from the RIS 14 and the console selector 42. The configurations of the host console 16, the first console 18, and the second console 20 are not necessarily required to be different from each other, but may be identical to each other.

The first image capturing apparatus 22 is a mammographic apparatus for capturing a radiation image of the breast 52 of a subject 50. As shown in FIG. 2, the first image capturing apparatus 22 comprises a radiation source housing 58 disposed on an upper end of an arm 56 that is swingably coupled to a base 54, an image capturing base 60 disposed on a lower end of the arm 56, and a compression plate 62 movably mounted on the arm 56 for movement toward and away from the image capturing base 60.

The radiation source housing 58 houses therein a radiation source 64 for emitting radiation X. The radiation source 64 has a tube voltage, tube current, and irradiation time of the radiation X controlled by a radiation source controller 66 (see FIG. 3), for irradiating the breast 52 of the subject 50 with radiation X at a given dosage level depending on the body region to be imaged.

Figure 4:
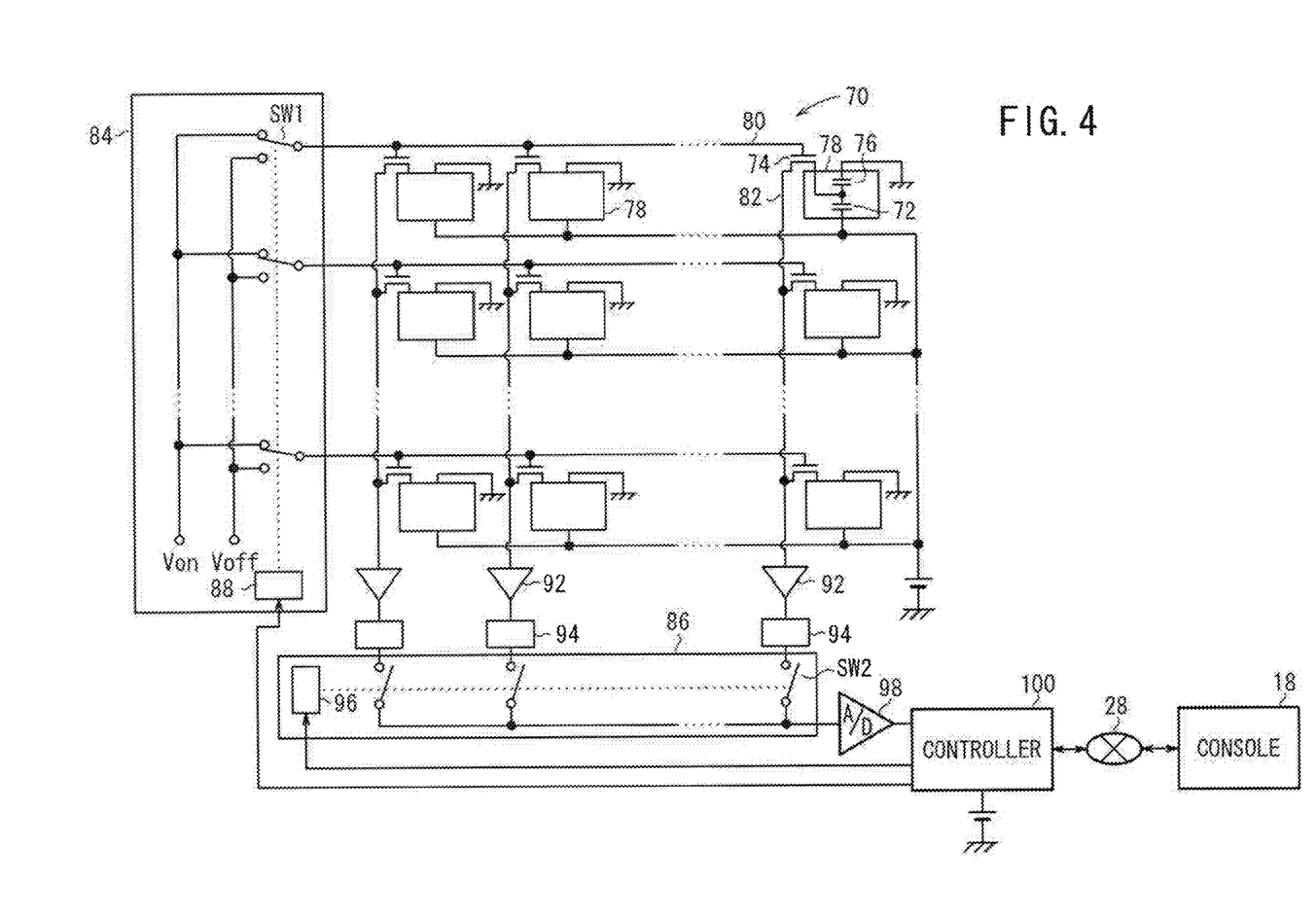
FIG. 4 is a block diagram of a circuit arrangement of a radiation conversion panel used in the radiation image capturing system.

The image capturing base 60 houses therein a radiation conversion panel 70, which has a circuit arrangement as shown in FIG. 4.

The radiation conversion panel 70 comprises an array of thin-film transistors (TFTs) 74 arranged in rows and columns, a photoelectric conversion layer 72 made of a material such as amorphous selenium (a-Se) for generating electric charges upon detection of radiation, the photoelectric conversion layer 72 being disposed on the array of TFTs 74, and an array of storage capacitors 76 connected to the photoelectric conversion layer 72. When radiation is applied to the radiation conversion panel 70, the photoelectric conversion layer 72 generates electric charges, and the generated electric charges are stored in the storage capacitors 76. Then, the TFTs 74 are turned on, each row at a time, to read electric charges from the storage capacitors 76 as an image signal. In FIG. 4, the photoelectric conversion layer 72 and one of the storage capacitors 76 are shown as making up one pixel 78, with the pixel 78 being connected to one of the TFTs 74. Details of the other pixels 78 are omitted from illustration. Since amorphous selenium tends to change in structure and lose functionality at high temperatures, amorphous selenium needs to be used within a certain temperature range. Therefore, some means for cooling the radiation conversion panel 70 should preferably be provided in the image capturing base 60.

The TFTs 74, which are connected to the respective pixels 78, are connected to respective gate lines 80 extending in parallel to the rows, and to respective signal lines 82 extending in parallel to the columns. The gate lines 80 are connected to a line scanning driver 84, whereas the signal lines 82 are connected to a multiplexer 86 serving as a reading circuit.

The gate lines 80 are supplied with control signals Von, Voff from the line scanning driver 84 for turning on and off the TFTs 74 along the rows. The line scanning driver 84 comprises a plurality of switches SW1 for switching between the gate lines 80, and an address decoder 88 for outputting a selection signal for selecting one of the switches SW1 at a time. The address decoder 88 is supplied with an address signal from a controller 100.

Further, the signal lines 82 are supplied with electric charges stored in the storage capacitors 76 of the pixels 78 through the TFTs 74 arranged in the columns. The electric charges supplied to the signal lines 82 are amplified by amplifiers 92 connected respectively to the signal lines 82. The amplifiers 92 are connected through respective sample and hold circuits 94 to the multiplexer 86. The multiplexer 86 comprises a plurality of switches SW2 for successively switching between the signal lines 82, and an address decoder 96 for outputting a selection signal for selecting one of the switches SW2 at a time. The address decoder 96 is supplied with an address signal from the controller 100. The multiplexer 86 has an output terminal connected to an A/D converter 98. A radiation image signal generated by the multiplexer 86, based on electric charges from the sample and hold circuits 94, is converted by the A/D converter 98 into a digital image signal representing radiation image information, which is supplied to the controller 100. The controller 100 supplies the acquired radiation image information through the in-house network 28 to the first console 18, which controls the first image capturing apparatus 22.

The TFTs 74, which function as switching elements, may be realized in combination with a CMOS (complementary metal-oxide semiconductor) image sensor or the like, or with other types of imaging devices. Still further, the TFTs 74 may be replaced by CCD (charge-coupled device) sensors, which transmit charges while shifting the charges by means of shift pulses, corresponding to the gate signals within the TFTs.

The second image capturing apparatus 24 is an upstanding image capturing apparatus for capturing a radiation image of the chest or the like of a subject 50. The second image capturing apparatus 24 comprises a radiation source 104 controlled by a radiation source controller 102, and an image capturing base 108 disposed in confronting relation to the radiation source 104. The image capturing base 108 has a slot 112, defined in a side wall thereof, through which a cassette 110 housing a stimulable phosphor panel P therein can be loaded into the image capturing base 108. The second image capturing apparatus 24 is controlled by the second console 20 through the in-house network 28.

The stimulable phosphor panel P comprises a support body and a stimulable phosphor layer disposed on the support body. The stimulable phosphor layer stores energy of the radiation X that is applied thereto. When the stimulable phosphor layer is irradiated with stimulating light, the stimulable phosphor layer emits stimulated light depending on the stored energy. When the stimulable phosphor layer is irradiated with erasing light, the stimulable phosphor layer discharges any remaining energy stored therein and can be reused.

The stimulable phosphor panel P housed in the cassette 110 is removable from the cassette 110 when a lid 114 on the cassette 110 is opened. A bar code 116, which records therein identification information, including a unique number for identifying the stimulable phosphor panel P housed in the cassette 110, the size of the stimulable phosphor panel P, the sensitivity of the stimulable phosphor panel P, etc., is applied to an outer surface of the cassette 110. The bar code 116 can be read by the bar-code reader 32 connected to the second console 20, or the bar-code reader 30 connected to the host console 16.

Figure 5:
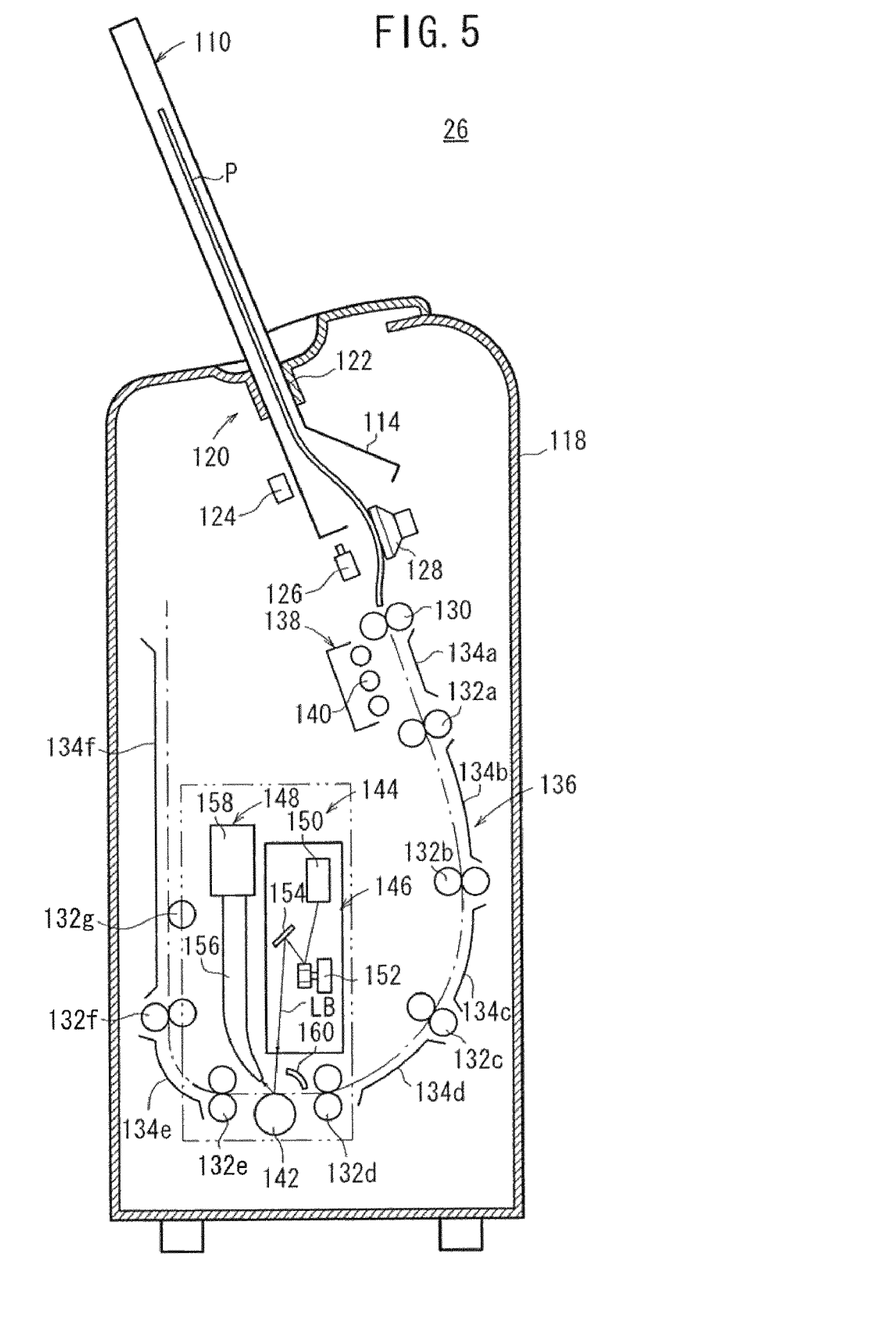
FIG. 5 is a vertical cross-sectional view of a reading apparatus of the radiation image capturing system.

Radiation image information recorded in the stimulable phosphor panel P is read by the reading apparatus 26, which is constructed as shown in FIG. 5. The reading apparatus 26 is controlled by the second console 20 through the in-house network 28.

The reading apparatus 26 includes a cassette loader 120 disposed in an upper portion of a casing 118 and having a loading slot 122 for receiving therein the cassette 110, which houses the stimulable phosphor panel P with recorded radiation image information. The casing 118 of the reading apparatus 26 accommodates therein, near the loading slot 122, a bar-code reader 124 for reading the identification information recorded in the bar code 116 on the cassette 110, an unlocking mechanism 126 for unlocking the lid 114 of the cassette 110, a suction cup 128 for attracting and removing the stimulable phosphor panel P from the cassette 110 at the time the lid 114 is opened, and a pair of nip rollers 130 for gripping and feeding the stimulable phosphor panel P removed by the suction cup 128.

The nip rollers 130 are followed by a plurality of feed rollers 132a through 132g and a plurality of guide plates 134a through 134f, which jointly make up a curved feed path 136. The curved feed path 136 extends downwardly from the cassette loader 120, extends substantially horizontally at a lowermost portion thereof, and then extends substantially vertically upwardly. The curved feed path 136 thus shaped is effective to make the reading apparatus 26 small in size.

Between the nip rollers 130 and the feed rollers 132a, an erasing unit 138 is disposed for erasing radiation image information remaining in the stimulable phosphor panel P, from which desired radiation image information has been read. The erasing unit 138 includes a plurality of erasing light sources 140, such as cold cathode-ray tubes or the like, for emitting erasing light.

A platen roller 142 is disposed between the feed rollers 132d, 132e, which are positioned in the lowermost portion of the curved feed path 136. The platen roller 142 is disposed beneath a scanning unit 144 for reading desired radiation image information recorded in the stimulable phosphor panel P.

The scanning unit 144 comprises a stimulator 146 for emitting a laser beam LB as stimulating light to scan the stimulable phosphor panel P, and a reader 148 for reading stimulated light emitted from the stimulable phosphor panel P when stimulated by the laser beam LB.

The stimulator 146 comprises a laser oscillator 150 for outputting the laser beam LB, a rotary polygon mirror 152 for deflecting the laser beam LB in a main scanning direction across the stimulable phosphor panel P, and a reflecting mirror 154 for reflecting the laser beam LB toward the stimulable phosphor panel P as the stimulable phosphor panel P passes over the platen roller 142.

The reader 148 comprises a light guide 156 having a lower end disposed near the stimulable phosphor panel P over the platen roller 142, and a photomultiplier 158 connected to an upper end of the light guide 156 for converting the stimulated light from the stimulable phosphor panel P into electric signals, which represent the radiation image information stored in the stimulable phosphor panel P. A light collecting mirror 160 for collecting the stimulated light from the stimulable phosphor panel P is disposed near the lower end of the light guide 156. The photomultiplier 158 supplies electric signals representing the radiation image information to the second console 20 through the in-house network 28.

In addition to the first image capturing apparatus 22, which is a mammographic apparatus, with the radiation conversion panel 70 loaded therein as shown in FIG. 4, another mammographic apparatus, which employs a cassette 110 housing a stimulable phosphor panel P therein as shown in FIG. 2, may also be connected to the in-house network 28. Similarly, in addition to the second image capturing apparatus 24, which employs the stimulable phosphor panel P shown in FIG. 2, an upstanding image capturing apparatus, which employs a radiation conversion panel 70 as shown in FIG. 4, may be connected to the in-house network 28. Moreover, a recumbent image capturing apparatus, which is capable of employing a radiation conversion panel 70 or a stimulable phosphor panel P therein, may be connected to the in-house network 28. Furthermore, image capturing apparatus having other specifications, such as a CT apparatus, an MR apparatus, etc., may also be connected to the in-house network 28. In addition, consoles (processors) for controlling such image capturing apparatus may also be connected to the in-house network 28.

The radiation image capturing system 10 according to the present invention is basically constructed as described above. Next, with reference to the flowcharts shown in FIGS. 6 and 7, operations (a method for supplying image capturing instruction information and a method for capturing a radiation image) of the radiation image capturing system 10 will be described below.

Figure 6:
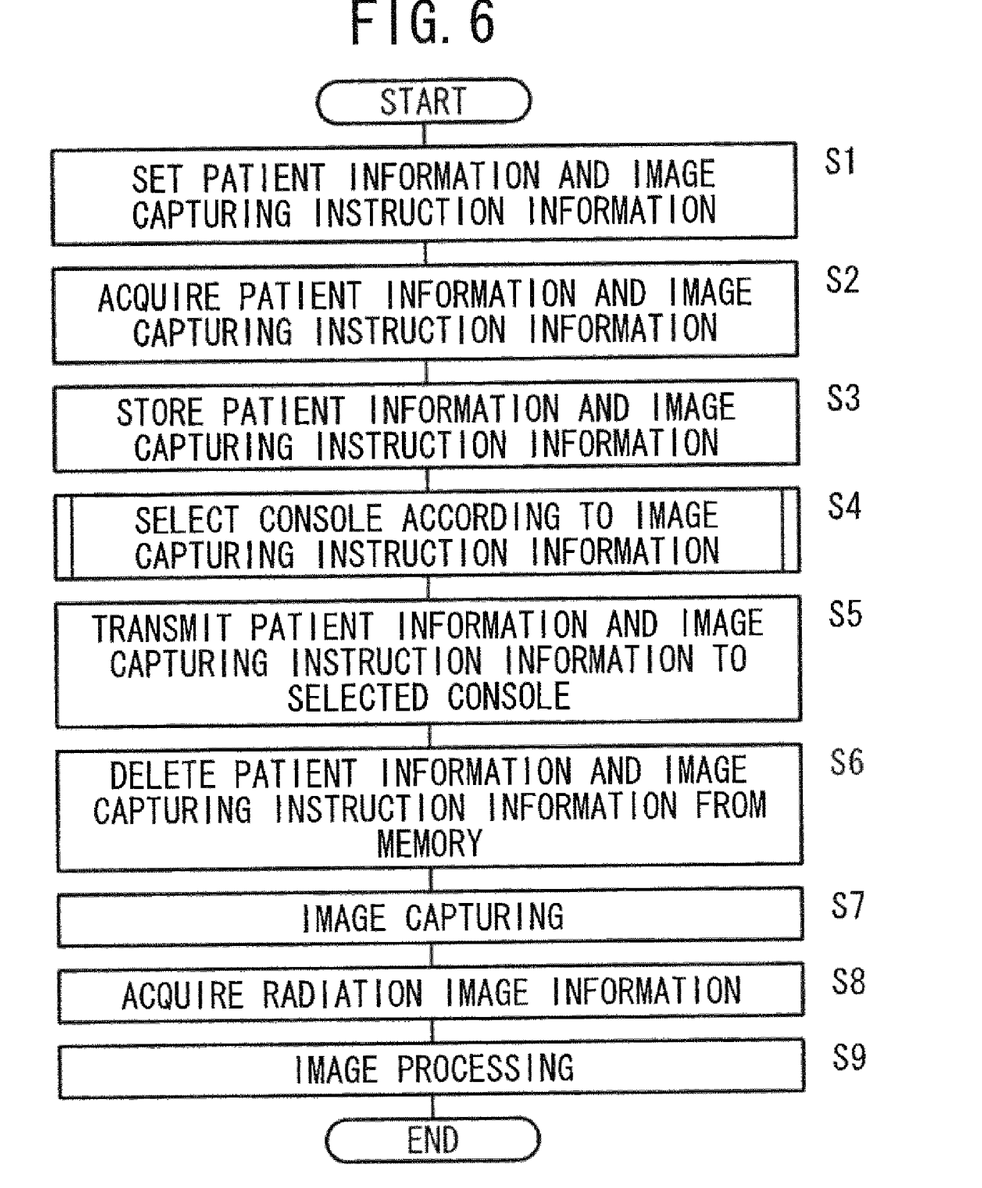
FIG. 6 is a flowchart for explaining operations of the system shown in FIG. 1.

First, patient information such as the name, gender, age, etc., of a patient is set using the HIS 12, and image capturing instruction information, such as a method for capturing a radiation image, a body region to be imaged, and an image capturing apparatus to be used to capture the radiation image, is set in relation to the patient information using the RIS 14 (step S1).

Through execution of a program, which is stored in a non-illustrated memory, the controller 34 of the host console 16, which is installed in the radiological department, acquires the patient information and the image capturing instruction information from the RIS 14 via the in-house network 28 (step S2). The radiological technician sets and changes the image capturing instruction information using the manual setting unit 36 of the host console 16. For example, the radiological technician may change from an image capturing apparatus set by the doctor using the RIS to another image capturing apparatus, which is better suited to the body region to be imaged and the condition of the patient. The image capturing instruction information setting unit 40 stores the acquired patient information and image capturing instruction information, or the image capturing instruction information which has been changed or newly set, in the image capturing instruction information memory 38 (step S3).

Then, the image capturing instruction information setting unit 40 reads the patient information and the image capturing instruction information from the image capturing instruction information memory 38. The console selector 42 selects the first console 18 for controlling the first image capturing apparatus 22, the second console 20 for controlling the second image capturing apparatus 24, or another console connected to the in-house network 28, according to the read image capturing instruction information (step S4).

Figure 7:
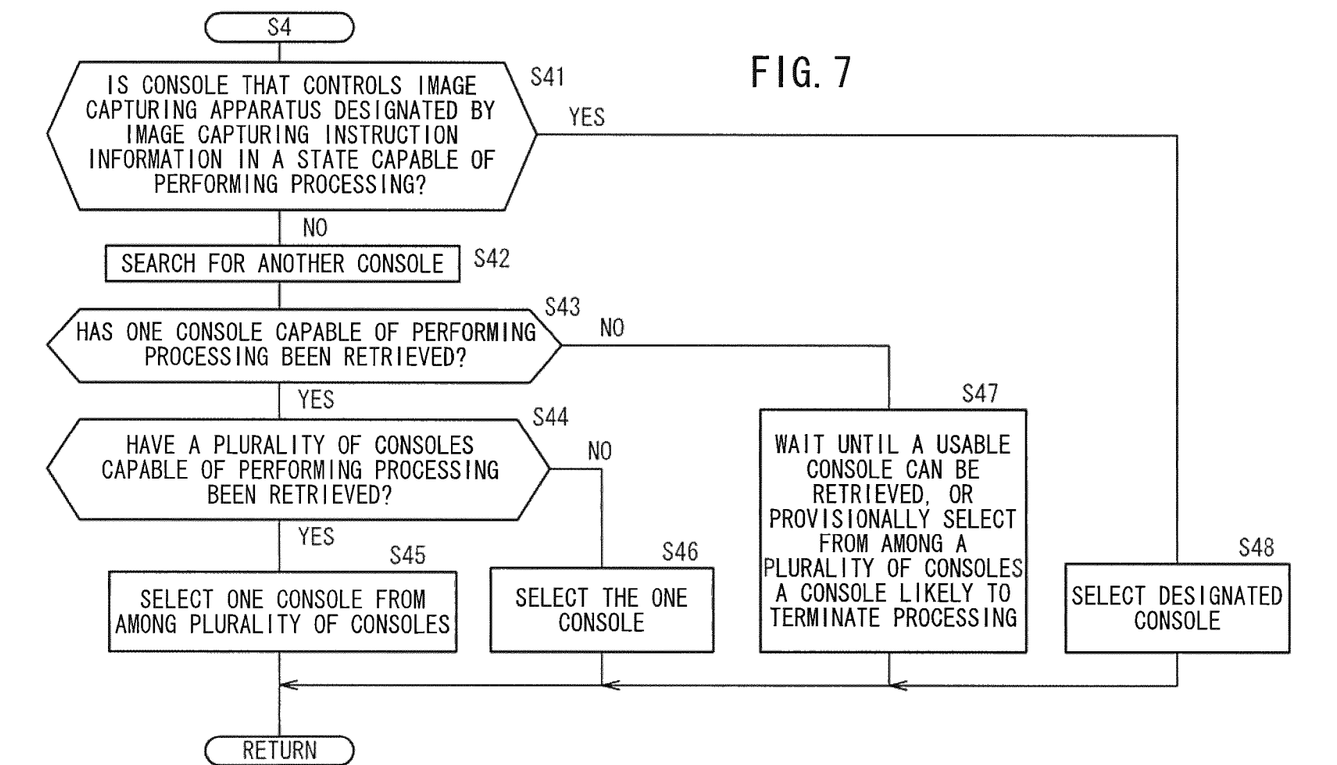
FIG. 7 is a flowchart for explaining further details of a process step S4 shown in FIG. 6.

At this time, the console selector 42 determines whether the processor, which is intended to control the image capturing apparatus that is indicated by the image capturing instruction information, is capable of performing its processing sequence or not (step S41). For example, if the processor is currently controlling an image capturing apparatus in order to perform an image capturing process, or is currently processing radiation image information acquired from the image capturing apparatus, and hence is unable to immediately perform a next cycle of processing sequence (NO in step S41), then the console selector 42 judges that the processor is incapable of performing its processing sequence. Furthermore, if the processor is suffering from a failure or the image capturing apparatus controlled by the processor is suffering a failure, the console selector 42 also judges that the processor is incapable of performing its processing sequence (NO in step S41). When the processor is judged as being incapable of performing its processing sequence, the console selector 42 searches for another processor, which is capable of capturing radiation image information according to the image capturing instruction information, and which is also capable of performing its processing sequence (step S42).

If, according to the searching process of step S42, one processor (console) in a state capable of carrying out its processing sequence can be retrieved (YES in step S43), and further, if a plurality of such processors can be retrieved (YES in step S44), then the console selector 42 selects, as the aforementioned other processor, one processor from among the plurality of processors that are in a state capable of carrying out processing (step S45).

At this time, concerning step S45, by performing any of the processes (1) through (5) listed below, the console selector 42 selects, as the other processor, the aforementioned one processor from among the plurality of processors, which are in a state capable of carrying out processing.

(1) In the case that a registration table, in which the first console 18, the second console 20, and other consoles are registered, is held by the host console 16, the console selector 42 selects one processor (console) according to a registration ordering or sequence of each of the consoles listed in the registration table.

(2) In the case that identification numbers for identifying the respective consoles are allocated to the first console 18, the second console 20, and other consoles, the console selector 42 selects one of the processors (consoles) according to its identification number. Further, if the identification number of each of the consoles is registered in the above-mentioned registration table, the console selector 42 can also select one of the processors according to the identification numbers in the registration table.

(3) In the case that all the processors are in a state capable of carrying out processing, the console selector 42 randomly selects one processor from among the plurality of processors.

(4) The console selector 42 selects one processor from among a plurality of processors, while considering the past frequency of use thereof.

(5) The console selector 42 selects one processor from among a plurality of processors by carrying out any of the aforementioned processes (1) through (4) with respect to processors, apart from the processor that controls the image capturing apparatus that performs the next intended image capturing process.

In step S44, in the case that only one processor could be retrieved (NO in step S44), the console selector 42 selects the one processor that could be retrieved, as the other processor (step S46).

Further, in step S43, in the case that a processor in a state capable of carrying out its processing sequence cannot be retrieved even though the searching process of step S42 was performed (NO in step S43), the console selector 42 either waits until a usable processor (i.e., a processor that is in a state capable of performing its processing sequence) can be retrieved, or alternatively, provisionally determines as the other processor a processor which can be projected to complete processing most rapidly from among the first console 18, the second console 20, and the other consoles (step S47).

Furthermore, in step S41, in the event that the console, which controls the image capturing apparatus designated by the image capturing instruction information, is in a state capable of carrying out its processing sequence, the designated console (processor) is selected (step S48).

After a processor capable of performing its processing sequence has been selected in accordance with the above-described steps S45 through S48, the controller 34 of the host console 16 sends the patient information and the image capturing instruction information to the first console 18, the second console 20, or to another console which has been selected (step S5), confirms that transmittal of the image capturing instruction information has been completed, and deletes the patient information and the image capturing instruction information from the image capturing instruction information memory 38 (step S6).

For example, if the image capturing instruction information represents an instruction to capture a chest image of the subject 50, then the console selector 42 selects the second console 20, for thereby controlling the second image capturing apparatus 24 to capture a chest image, and sends the patient information and the image capturing instruction information to the second console 20. If the image capturing instruction information represents an instruction for capturing an image of the breast 52 of the subject 50, then the console selector 42 selects the first console 18, for thereby controlling the first image capturing apparatus 22 to capture an image of the breast 52, and sends the patient information and the image capturing instruction information to the first console 18.

Another console selection mode will be described below. For example, when the subject 50 whose chest image is to be captured uses a wheelchair, then the subject 50 cannot be positioned with respect to the image capturing base 108 of the second image capturing apparatus 24, which is shown in FIG. 2. In this case, if an image capturing apparatus, which is capable of handling the subject 50 who uses a wheelchair, is connected to the in-house network 28, then the console selector 42 selects that image capturing apparatus according to the patient information, and sends the image capturing instruction information to a console that controls the image capturing apparatus.

According to still another console selection mode, an image of a body region of the subject 50 is captured by the first image capturing apparatus 22, whereas an image of another body region of the subject 50 is captured by the second image capturing apparatus 24. In this case, the console selector 42 selects the corresponding consoles according to the image capturing instruction information for the body regions to be imaged, and sends the selected items of patient information and image capturing instruction information respectively to the consoles.

If the host console 16 serves as a processor capable of performing processing sequences for a plurality of image capturing apparatus having different specifications, then the host console 16 may be selected as the console, instead of the first console 18 or the second console 20, in order to perform processing sequences for the first image capturing apparatus 22 or the second image capturing apparatus 24.

The console, to which the patient information and the image capturing instruction information have been sent, performs a process for capturing radiation image information using the image capturing apparatus under its control (step S7), and according to the image capturing instruction information.

First, a process of capturing radiation image information of the breast 52 of the subject 50 with the first image capturing apparatus 22 under the control of the first console 18 will be described below.

When the first console 18 receives image capturing instruction information from the host console 16, the first console 18 sets image capturing conditions, including a tube voltage, a tube current, and an irradiation time, which are contained in the image capturing instruction information in the radiation source controller 66 of the first image capturing apparatus 22.

The radiological technician operates the first image capturing apparatus 22 to prepare the first image capturing apparatus for carrying out an image capturing process. More specifically, the radiological technician turns the arm 56 to set an image capturing direction, and then positions the breast 52 of the subject 50 on the image capturing base 60. The radiological technician moves the compression plate 62 toward the image capturing base 60, thereby positioning the breast 52 securely in place on the image capturing base 60.

Then, the radiological technician operates an image capturing switch (not shown) to initiate an image capturing process. The radiation source controller 66 controls the radiation source 64 according to the set image capturing conditions to apply radiation X to the breast 52 through the compression plate 62. Radiation X that has passed through the breast 52 is applied to the radiation conversion panel 70.

The radiation X is converted into electric signals by the photoelectric conversion layer 72 made up of the pixels 78 of the radiation conversion panel 70 (see FIG. 4). The electric signals are stored as electric charges in the storage capacitors 76. The stored electric charges, which represent radiation image information of the patient 50, typically a breast 52 of the patient 50, are read from the storage capacitors 76 according to address signals, which are supplied from the controller 100 to the line scanning driver 84 and the multiplexer 86.

Specifically, in response to the address signal supplied from the controller 100, the address decoder 88 of the line scanning driver 84 outputs a selection signal to select one of the switches SW1, which supplies the control signal Von to the gates of the TFTs 74 connected to the gate line 80 corresponding to the selected switch SW1. In response to the address signal supplied from the controller 100, the address decoder 96 of the multiplexer 86 outputs a selection signal in order to successively turn on the switches SW2 to switch between the signal lines 82, for thereby reading, through the signal lines 82, electric charges that are stored in the storage capacitors 76 of the pixels 78 connected to the selected gate line 80.

The electric charges read from the storage capacitors 76 of the pixels 78 connected to the selected gate line 80 of the radiation conversion panel 70 are amplified by the respective amplifiers 92, sampled by the sample and hold circuits 94, and supplied to the multiplexer 86. Based on the supplied electric charges, the multiplexer 86 generates and supplies a radiation image signal to the A/D converter 98, which converts the radiation image signal into digital signals. The digital signals, which represent the radiation image information, are transmitted from the controller 100 to the first console 18 through the in-house network 28 (step S8).

Similarly, the address decoder 88 of the line scanning driver 84 successively turns on the switches SW1 to switch between the gate lines 80 according to the address signal supplied from the controller 100. The electric charges stored in the storage capacitors 76 of the pixels 78 connected to the successively selected gate lines 80 are read through the signal lines 82, processed by the multiplexer 86, and converted into digital signals by the A/D converter 98, which are transmitted from the controller 100 to the first console 18 through the in-house network 28 (step S8).

The first console 18 processes the radiation image information represented by the received digital signals depending on the specifications of the first image capturing apparatus 22 (step S9). Then, the first console 18 displays a radiation image based on the processed radiation image information in order for the radiological technician to confirm the radiation image, and then transmits the radiation image information to the viewer 15 through the in-house network 28. The doctor diagnostically interprets the radiation image that is displayed by the viewer 15 based on the radiation image information. If the first console 18 is currently processing other radiation image information, which has already been received thereby, then the console selector 42 of the host console 16 searches for another processor, which is capable of carrying out processing, and sends the radiation image information acquired from the first image capturing apparatus 22 to the other processor, which was found and retrieved, so that the other processor can process the radiation image information.

A process of capturing a chest image of the subject 50 with the second image capturing apparatus 24 controlled by the second console 20 will be described below.

When the second console 20 receives the image capturing instruction information from the host console 16, the second console 20 sets image capturing conditions, including a tube voltage, a tube current, and an irradiation time, which are contained in the image capturing instruction information in the radiation source controller 102 of the second image capturing apparatus 24.

The radiological technician uses the bar-code reader 32 connected to the second console 20 to read the bar code 116 applied to the cassette 110, thereby acquiring identification information, including a unique number for identifying the stimulable phosphor panel P housed in the cassette 110, the size of the stimulable phosphor panel P, the sensitivity of the stimulable phosphor panel P, etc.

Next, after having loaded the cassette 110 into the slot 112 of the second image capturing apparatus 24, the radiological technician operates an image capturing switch (not shown) to initiate an image capturing process. The radiation source controller 102 controls the radiation source 104 according to the set image capturing conditions in order to apply radiation X to the subject 50. Radiation X that has passed through the subject 50 is applied to the stimulable phosphor panel P housed in the cassette 110. As a result, radiation image information of the subject 50 is recorded in the stimulable phosphor panel P.

The radiological technician then removes the cassette 110, which houses therein the stimulable phosphor panel P with the recorded radiation image information, from the second image capturing apparatus 24, and thereafter loads the cassette 110 into the cassette loader 120 of the reading apparatus 26.

When the cassette 110 has been loaded into the cassette loader 120, the bar-code reader 124 in the cassette loader 120 reads the bar code 116 applied to the cassette 110 in order to acquire the identification information, including the unique number, the size, the sensitivity, etc., of the stimulable phosphor panel P. The acquired identification information is compared with the identification information read by the bar-code reader 32 connected to the second console 20 in order to confirm a correspondence between the subject 50 and the radiation image information.

After the identification information is read, the unlocking mechanism 126 is actuated to unlock and open the lid 114. The suction cup 128 attracts the stimulable phosphor panel P, takes the stimulable phosphor panel P out of the cassette 110, and feeds the stimulable phosphor panel P between the nip rollers 130. The stimulable phosphor panel P, which is gripped by the nip rollers 130, is subsequently fed through the curved feed path 136, made up of the feed rollers 132$a$ through 132$g$ and the guide plates 134$a$ through 134$f$, to a position beneath the scanning unit 144.

Beneath the scanning unit 144, the stimulable phosphor panel P is fed substantially horizontally in an auxiliary scanning direction by the feed rollers 132$d$, 132$e$. At the same time, the laser beam LB output from the laser oscillator 150 of the stimulator 146 is reflected and deflected by the polygon mirror 152, which rotates at a high speed, and the laser beam LB is guided by the reflecting mirror 154 toward the stimulable phosphor panel P whose lower surface is supported by the platen roller 142, for thereby scanning the stimulable phosphor panel P in a main scanning direction, which is perpendicular to the auxiliary scanning direction.

By being irradiated with the laser beam LB, the stimulable phosphor panel P is stimulated to emit stimulated light representative of the radiation image information recorded therein. The stimulated light is applied, either directly or via the light collecting mirror 160, to the lower end of the light guide 156, which is disposed near the stimulable phosphor panel P and extends in the main scanning direction. The stimulated light, which has entered into the light guide 156, is repeatedly reflected within the light guide 156 and guided to the photomultiplier 158. The photomultiplier 158 converts the stimulated light into electric signals representative of the radiation image information recorded in the stimulable phosphor panel P. In this manner, the radiation image information recorded in the stimulable phosphor panel P is read by the scanning unit 144 of the reading apparatus 26 (step S8).

The radiation image information thus read by the scanning unit 144 is transmitted to the second console 20 through the in-house network 28. The second console 20 processes the received radiation image information depending on the specifications of the second image capturing apparatus 24 (step S9). The second console 20 displays a radiation image based on the processed radiation image information in order for the radiological technician to be able to confirm the radiation image. Then, the second console 20 transmits the radiation image information to the viewer 15 through the in-house network 28. The doctor diagnostically interprets a radiation image that is displayed by the viewer 15 based on the radiation image information. If the second console 20 is processing other radiation image information, which has already been received thereby, then the console selector 42 of the host console 16 searches for another processor that is capable of carrying out processing, and sends the radiation image information acquired from the second image capturing apparatus 24 to the other processor, that has been found and retrieved, so that the other processor can process the radiation image information.

Although a certain preferred embodiment of the present invention has been shown and described in detail, it should be understood that various changes and modifications may be made to the embodiment without departing from the scope of the invention as set forth in the appended claims.

For example, the aforementioned radiation conversion panel 70 makes up a radiation detector, which converts the radiation dose of the irradiated radiation directly into electric signals through the photoelectric conversion layer 72. However, in place of this structure, a radiation detector in which irradiated radiation is converted initially into visible light by a scintillator, and thereafter, the visible light is converted into electric signals using a solid-state detecting device formed from amorphous silicon (a-Si) or the like, may also be used (see, Japanese Patent No. 3494683).

Further, the radiation image information can be obtained using a light readout type of radiation detector. With such a light readout type of radiation detector, radiation is radiated onto respective solid state detecting devices arranged in a matrix form, and an electrostatic latent image corresponding to the irradiation dose is stored cumulatively in the solid state detecting devices. When the electrostatic latent image is read, reading light is radiated onto the radiation detector, and the generated current values are acquired as radiation image information. Further, by irradiating the radiation detector with erasing light, the radiation image information in the form of a residual electrostatic latent image can be erased and the radiation detector can be reused (see, Japanese Laid-Open Patent Publication No. 2000-105297).

Furthermore, in the present embodiment, a case has been described in which patient information is set in the HIS 12 by a doctor, image capturing instruction information is set in the RIS 14 by a doctor or a technician, and such information is supplied to the host console 16 over an in-house hospital network 28, and moreover, wherein such information is supplied from the host console 16 to the first console 18 or the second console 20. However, in place of this configuration, the patient information and image capturing instruction information may also be set directly in the host console 16, the first console 18 or the second console 20, or alternatively, the patient information and image capturing instruction information may be set either by the HIS 12 or the RIS 14.

What is claimed is:

1. A radiation image capturing system comprising:
   a plurality of image capturing apparatus having different specifications for capturing a radiation image of a subject;
   a plurality of processors having specifications corresponding to the specifications of the image capturing apparatus, for controlling the image capturing apparatus and processing radiation image information acquired from the image capturing apparatus; and
   a supply apparatus for supplying image capturing instruction information for the image capturing apparatus to one of the processors, which is selected depending on the specifications of the image capturing apparatus.

2. A radiation image capturing system according to claim 1, wherein the image capturing instruction information comprises information of the subject.

3. A radiation image capturing system according to claim 1, wherein the image capturing instruction information comprises image capturing conditions under which the image capturing apparatus captures the radiation image of the subject.

4. A radiation image capturing system according to claim 1, wherein the supply apparatus includes storage means for storing the image capturing instruction information to be supplied to the processors.

5. A radiation image capturing system according to claim 1, wherein the supply apparatus is one of the processors.

6. A radiation image capturing system comprising:
   a plurality of image capturing apparatus having different specifications for capturing a radiation image of a subject;
   a plurality of processors having specifications corresponding to the specifications of the image capturing apparatus, for controlling the image capturing apparatus and processing radiation image information acquired from the image capturing apparatus; and
   a supply apparatus for selecting one of the processors having specifications that correspond to the specifications of the image capturing apparatus, and which is capable of performing processing sequences for the image capturing apparatus, and supplying image capturing instruction information for the image capturing apparatus to the selected one of the processors.

7. A radiation image capturing system according to claim 6, wherein the image capturing instruction information comprises information of the subject.

8. A radiation image capturing system according to claim 6, wherein the image capturing instruction information comprises image capturing conditions under which the image capturing apparatus captures the radiation image of the subject.

9. A radiation image capturing system according to claim 6, wherein the supply apparatus selects one of the processors depending on a processing state thereof.

10. A radiation image capturing system according to claim 6, wherein the supply apparatus selects one of the processors depending on a failure state thereof.

11. A radiation image capturing system according to claim 6, wherein the supply apparatus includes storage means for storing the image capturing instruction information to be supplied to the processors.

12. A radiation image capturing system according to claim 6, wherein the supply apparatus is one of the processors.

13. A radiation image capturing system according to claim 6, wherein the supply apparatus determines whether the processor, which controls the image capturing apparatus designated by the image capturing instruction information, is in a state capable of performing processing, and if the processor is in a state incapable of performing processing, the supply apparatus searches for another processor that is in a state capable of performing processing.

14. A radiation image capturing system according to claim 13, wherein when the supply apparatus is capable of retrieving a plurality of processors that are in a state capable of performing processing, the supply apparatus selects one processor from among the plurality of processors as the other processor, or alternatively, when the supply apparatus is capable of retrieving only one processor that is in a state capable of performing processing, the supply apparatus selects the one processor as the other processor.

15. A radiation image capturing system according to claim 13, wherein when the supply apparatus is incapable of retrieving a processor that is in a state capable of performing processing, the supply apparatus waits until a processor that is in a state capable of performing processing can be retrieved, or alternatively, provisionally determines, as the other processor, a processor which can be projected to complete processing most rapidly from among a plurality of processors.

16. A supply apparatus for supplying image capturing instruction information, wherein, in the case that a plurality of image capturing apparatus having different specifications for capturing a radiation image of a subject, and a plurality of processors having specifications corresponding to the specifications of the image capturing apparatus, for controlling the image capturing apparatus and processing radiation image information acquired from the image capturing apparatus, are provided,
the supply apparatus selects the processors depending on the specifications of the image capturing apparatus, and supplies image capturing instruction information pertaining to the image capturing apparatus to the selected processors.

17. A supply apparatus for supplying image capturing instruction information, wherein, in the case that a plurality of image capturing apparatus having different specifications for capturing a radiation image of a subject, and a plurality of processors having specifications corresponding to the specifications of the image capturing apparatus, for controlling the image capturing apparatus and processing radiation image information acquired from the image capturing apparatus, are provided,
the supply apparatus selects one of the processors depending on the specifications of the image capturing apparatus, and further which is in a state capable of performing processing, and supplies image capturing instruction information pertaining to the image capturing apparatus to the selected one processor.

18. A non-transitory computer-readable storage medium embodied with a program, wherein, in the case that a plurality of image capturing apparatus having different specifications for capturing a radiation image of a subject, and a plurality of processors having specifications corresponding to the specifications of the image capturing apparatus, for controlling the image capturing apparatus and processing radiation image information acquired from the image capturing apparatus, are provided,
the program is executed in a supply apparatus for supplying, from the supply apparatus, image capturing instruction information pertaining to the image capturing apparatus to the processors, the program comprising:
a step of selecting the processors depending on the specifications of the image capturing apparatus, and
a step of supplying, from the supply apparatus, image capturing instruction information pertaining to the image capturing apparatus to the selected processor.

19. A non-transitory computer-readable storage medium embodied with a program, wherein, in the case that a plurality of image capturing apparatus having different specifications for capturing a radiation image of a subject, and a plurality of processors having specifications corresponding to the specifications of the image capturing apparatus, for controlling the image capturing apparatus and processing radiation image information acquired from the image capturing apparatus, are provided,
the program is executed in a supply apparatus for supplying, from the supply apparatus, image capturing instruction information pertaining to the image capturing apparatus to the processors, the program comprising:
a step of selecting one of the processors depending on the specifications of the image capturing apparatus, and further which is in a state capable of performing processing; and
a step of supplying, from the supply apparatus, image capturing instruction information pertaining to the image capturing apparatus to the selected one processor.

20. A method for supplying image capturing instruction information, wherein, in the case that a plurality of image capturing apparatus having different specifications for capturing a radiation image of a subject, and a plurality of processors having specifications corresponding to the specifications of the image capturing apparatus, for controlling the image capturing apparatus and processing radiation image information acquired from the image capturing apparatus, are provided, the method comprising the steps of:
selecting the processors depending on the specifications of the image capturing apparatus; and
supplying, from the supply apparatus, image capturing instruction information pertaining to the image capturing apparatus to the selected processor.

21. A method for supplying image capturing instruction information, wherein, in the case that a plurality of image capturing apparatus having different specifications for capturing a radiation image of a subject, and a plurality of processors having specifications corresponding to the specifications of the image capturing apparatus, for controlling the image capturing apparatus and processing radiation image information acquired from the image capturing apparatus, are provided, the method comprising the steps of:
selecting one of the processors depending on the specifications of the image capturing apparatus, and further which is in a state capable of performing processing; and
supplying, from the supply apparatus, image capturing instruction information pertaining to the image capturing apparatus to the selected one processor.

22. A method for capturing a radiation image, wherein, in the case that a plurality of image capturing apparatus having different specifications, and a plurality of processors having specifications corresponding to the specifications of the image capturing apparatus, are provided, the method comprising the steps of:

selecting the processors depending on the specifications of the image capturing apparatus;

supplying image capturing instruction information from a supply apparatus to the selected processor;

capturing a radiation image of a subject using the image capturing apparatus, by the processor controlling the image capturing apparatus according to the image capturing instruction information; and acquiring radiation image information from the image capturing apparatus and performing image processing thereon using the processor.

23. A method for capturing a radiation image, wherein, in the case that a plurality of image capturing apparatus having different specifications, and a plurality of processors having specifications corresponding to the specifications of the image capturing apparatus, are provided, the method comprising the steps of:

selecting one of the processors depending on the specifications of the image capturing apparatus, and further which is in a state capable of performing processing, and supplying, from the supply apparatus, image capturing instruction information to the selected one processor;

capturing a radiation image of a subject using the image capturing apparatus, by the one processor controlling the image capturing apparatus according to the image capturing instruction information; and acquiring radiation image information from the image capturing apparatus and performing image processing thereon using the one processor.

* * * * *